United States Patent
Nikolaidis et al.

(10) Patent No.: US 12,339,287 B2
(45) Date of Patent: Jun. 24, 2025

(54) METHOD FOR MANUFACTURING AN ELECTROCHEMICAL SENSOR

(71) Applicant: Heraeus Deutschland Gmbh & Co. KG, Hanau (DE)

(72) Inventors: Ilias Nikolaidis, Hanau (DE); Andreas Reisinger, Hanau (DE); Stefan Schibli, Hanau (DE); Heiko Specht, Hanau (DE); Jörg-Martin Gebert, Hanau (DE)

(73) Assignee: Heraeus Medevio GmbH & Co. KG, Hanau (DE)

( * ) Notice: Subject to any disclaimer, the term of this patent is extended or adjusted under 35 U.S.C. 154(b) by 565 days.

(21) Appl. No.: 17/030,555

(22) Filed: Sep. 24, 2020

(65) Prior Publication Data

US 2021/0096136 A1 Apr. 1, 2021

(30) Foreign Application Priority Data

Sep. 27, 2019 (EP) .................................... 19200065

(51) Int. Cl.
*G01N 33/66* (2006.01)
*A61B 5/1473* (2006.01)
(Continued)

(52) U.S. Cl.
CPC .......... *G01N 33/66* (2013.01); *A61B 5/14735* (2013.01); *B41M 1/22* (2013.01); *C09D 11/52* (2013.01); *A61B 2562/125* (2013.01)

(58) Field of Classification Search
CPC ................ G01N 33/66; G01N 27/3271; A61B 5/14735; A61B 5/1468; A61B 5/14539;
(Continued)

(56) References Cited

U.S. PATENT DOCUMENTS

| 6,103,033 A | 8/2000 | Say et al. |
| 7,922,883 B2 * | 4/2011 | Petyt ...................... C12Q 1/006 |
| | | 204/403.01 |

(Continued)

FOREIGN PATENT DOCUMENTS

| JP | 2008510506 A * | 4/2008 | .......... A61B 5/1468 |
| WO | 99/45375 | 9/1999 | |

(Continued)

OTHER PUBLICATIONS

Translation of JP-2008510506-A (Year: 2008).*

(Continued)

*Primary Examiner* — Jeffrey T Carley
(74) *Attorney, Agent, or Firm* — Dicke, Billig & Czaja, PLLC

(57) ABSTRACT

One aspect relates to a process for manufacturing an electrochemical sensor, including moving a metal wire from a wire feed unit to a wire pick-up unit, the moving wire passing at least one printer $P_{cond}$ which is located in between the wire feed and wire pick-up units, and printing an ink which includes electrically conductive particles by the printer $P_{cond}$ onto discrete arrays of an electrically insulating polymer coating which is present on the metal wire.

11 Claims, 3 Drawing Sheets

(51) Int. Cl.
*B41M 1/22* (2006.01)
*C09D 11/52* (2014.01)
(58) Field of Classification Search
CPC ............ A61B 5/14542; A61B 5/14546; A61B 5/1486; A61B 2562/125; A61B 5/14532; B41M 1/22; C09D 11/52; C12Q 1/006
See application file for complete search history.

(56) References Cited

U.S. PATENT DOCUMENTS

| | | | |
|---|---|---|---|
| 9,907,497 | B2 | 3/2018 | Simpson et al. |
| 2003/0188427 | A1* | 10/2003 | Say .................... A61B 5/14532 29/595 |
| 2011/0230735 | A1* | 9/2011 | Wolfe ................ A61B 5/14503 204/403.14 |
| 2012/0088993 | A1 | 4/2012 | Buck et al. |
| 2013/0245412 | A1* | 9/2013 | Rong ................. A61B 5/14532 600/347 |
| 2014/0275896 | A1 | 9/2014 | Hughes et al. |
| 2018/0042529 | A1 | 2/2018 | Simpson et al. |
| 2018/0199873 | A1 | 7/2018 | Wang et al. |
| 2019/0261907 | A1* | 8/2019 | Brister ............... A61B 5/14865 |
| 2021/0015407 | A1* | 1/2021 | Bohm .................... C09J 181/00 |

FOREIGN PATENT DOCUMENTS

| | | | | |
|---|---|---|---|---|
| WO | WO-2004039897 | A2 * | 5/2004 | ......... A61B 5/14532 |
| WO | 2011/003039 | | 1/2011 | |

OTHER PUBLICATIONS

A. Heller and B. Feldman, "Electrochemical Glucose Sensors and Their Applications in Diabetes Management", Chem. Rev., 2008, 108, pp. 2482-2505.

E.W. Nery et al., "Electrochemical Glucose Sensing: Is There Still Room For Improvement?", Analyt. Chem., 2016, 88, pp. 11271-11282.

R. Urbas et al., "Pad Printing", pp. 263-278, in "Printing on Polymers: Fundamentals and Applications", Ed.: J. Izdebska, S. Thomas, Elsevier, 2016.

A. Soleimani-Gorgani, "Inkjet Printing", pp. 231-246, in "Printing on Polymers: Fundamentals and Applications", Ed.: J. Izdebska, S. Thomas, Elsevier, 2016; and J. Li et al., Lab Chip, 15, 2015, pp. 2538-2558.

J. Li et al., "Inkjet Printing for Biosensor Fabrication: Combining Chemistry and Technology for Advanced Manufacturing", Lab Chip, 15, 2015, pp. 2538-2558.

* cited by examiner

METHOD FOR MANUFACTURING AN ELECTROCHEMICAL SENSOR

CROSS-REFERENCE TO RELATED APPLICATIONS

This Utility patent application claims priority to European Application No. 19 200 065.1, filed on Sep. 27, 2019, which is incorporated herein by reference.

TECHNICAL FIELD

One aspect relates to a method for manufacturing an electrochemical sensor (e.g. a glucose sensor) and to a sensor having a specific electrode arrangement which is obtainable by the manufacturing method.

BACKGROUND

Electrochemical sensors can be used for measuring the concentration of specific analytes (such as glucose) which might be related to specific disorders (e.g. a metabolic disorder such as diabetes). Electrochemical sensors include two or more electrodes (working electrode, reference electrode, counter electrode). In a two-electrode set-up, the second electrode represents both the reference and the counter electrode. Measuring accuracy can be improved if a three-electrode set-up (i.e. separate reference and counter electrodes) is used. In the presence of the analyte to be detected, an electrochemical reaction takes place at the working electrode. The measurable response is either an electrical current due to the redox reaction (amperometric sensor) or the change in electrode potential (potentiometric sensor).

Both enzyme-based and non-enzymatic glucose sensors are known. Most commonly, oxidase enzymes (such as glucose oxidase) are used. The enzyme may convert the analyte to gluconolactone and hydrogen peroxide ($H_2O_2$), and $H_2O_2$ can be oxidized at the working electrode. The enzyme is typically present in a polymer matrix which is applied on the working electrode.

Electrochemical glucose sensors are reviewed by A. Heller and B. Feldman, "*Electrochemical Glucose Sensors and Their Applications in Diabetes Management*", Chem. Rev., 2008, 108, pp. 2482-2505; and E. W. Nery et al., "*Electrochemical Glucose Sensing: Is There Still Room For Improvement?*", Analyt. Chem., 2016, 88, pp. 11271-11282.

One type of glucose sensor which is used for continuous glucose monitoring is a wire-based sensor. A metal wire (e.g. a noble metal wire) which acts as the working electrode is coated with an electrically insulating polymer coating which in turn is coated with an electrically conductive layer (e.g. a layer containing Ag/AgCl) acting as the reference/counter electrode. Both the insulating polymer coating and the conductive layer (in the form of a conductive ink) are typically applied by conventional coating methods such as die coating or immersion coating. For each coating step, several runs are needed until the desired coating thickness is achieved. After these coating steps, the insulating polymer coating and the conductive Ag/AgCl-containing layer are removed in pre-defined areas via laser ablation, thereby exposing a pre-defined area of the metal wire and making the metal wire accessible to the analyte to be detected. However, this results in a loss of silver-containing material and is therefore adversely affecting process efficiency. Furthermore, it still remains very challenging to carry out laser ablation at such a high accuracy level that the Ag/AgCl-containing material is exclusively removed in the pre-defined areas. On the exposed area of the metal wire, a polymer membrane is typically provided and an enzyme might be immobilized therein. Typically, the wire-based sensor obtained by the method has a two-electrode-configuration (the exposed area of the metal wire representing the working electrode and the "non-structured" single-piece Ag/AgCl-containing layer representing both the reference and counter electrode). For providing a three-electrode configuration, it would be necessary to subject the Ag/AgCl-containing layer to a structuring treatment, e.g. by laser ablation. However, this additional treatment step would make the manufacturing process even more complex and time consuming and may result in a further loss of silver-containing material.

WO 2011/003039 A2 describes a continuous analyte sensor, including an elongated core including a working electrode; an insulating layer covering at least a portion of the elongated core; a conductive layer including a reference electrode or a counter electrode, wherein the conductive layer covers at least a portion of the insulating layer; and a membrane covering at least a portion the working electrode.

US 2018/0042529 A1 describes a method of making a sensor device configured for implantation in a host. The method includes forming a piercing tip on a sensor unit, the sensor unit including a sensor body, at least one electrode, and a membrane covering at least a portion of the at least one electrode; wherein the membrane is applied to the sensor unit prior to forming the piercing tip on the sensor unit.

It is known that pad printing can be used for printing on uneven or curved surfaces. Pad printing is an indirect gravure printing method. On a printing plate (also known as cliché), the ink is provided and then picked-up by a flexible pad (e.g. a silicone pad) and transferred to the substrate on which an image shall be printed. Typically, the printing plate includes depressions or wells (e.g. formed by etching) which are filled with the printing ink. Due to its flexibility, the pad can adapt to both the depression when picking up the ink and the surface contour of the object when printing the image.

Different types of cliché s and pads are known. The cliché might be a flat plate with etched wells. In rotary pad printing, both the cliché and the pad are cylindrical and rotate in opposite directions. The pad roll picks up the ink and transfers it to the object to be printed. It is also known to use a carousel-type pad printer wherein the pads are positioned in a circular holder. The ink is provided in circular arranged wells. While one of the pads of the circular pad holder picks up ink from one of the ink-containing wells, another pad is printing the ink onto the substrate. During one revolution of the circular pad holder, each of the pads picks up ink from the ink reservoir and prints the ink onto the substrate.

Details about pad printing are described e.g. by R. Urbas et al., "*Pad Printing*", pp. 263-278, in "*Printing on Polymers: Fundamentals and Applications*", Ed.: J. Izdebska, S. Thomas, Elsevier, 2016.

It is known that nozzle printing (i.e. ejecting the printing ink through a printing nozzle) such as inkjet printing or arerosol jet printing might be used for manufacturing of printed electronics, see e.g. A. Soleimani-Gorgani, "*Inkjet Printing*", pp. 231-246, in "*Printing on Polymers: Fundamentals and Applications*", Ed.: J. Izdebska, S. Thomas, Elsevier, 2016; and J. Li et al., Lab Chip, 15, 2015, pp. 2538-2558.

As also known to the skilled person, two modes of operation might be used for inkjet printing, which are continuous inkjet printing ("CIJ printing") and drop-on-demand inkjet printing ("DOD" inkjet printing).

In a continuous inkjet printer, ink droplets are constantly generated, controlled by a high-pressure pump vibrating the nozzle with a piezoelectric crystal. The generated ink droplets are selectively charged by signals from the printer. Charged droplets are deflected into a gutter for recirculation, while the uncharged droplets are ejected onto the substrate to form an image.

Different from a continuous inkjet printer, a drop-on-demand (DOD) inkjet printer ejects the ink only when it is required. Known DOD inkjet printers are e.g. thermal inkjet printers and piezoelectric inkjet printers. In a thermal inkjet printer, the ink in the ink chamber is rapidly heated up to a vaporization temperature. Due to vaporisation, a bubble is promptly generated at the surface of a heating element, causing a pressure pulse to eject the ink droplets through the nozzle. In a piezoelectric printer, a piezo-ceramic material is used for generating ink droplets. In response to an electric impulse, the piezo-ceramic material deforms, thereby generating a pressure wave by which the ink is ejected through the printing nozzle.

SUMMARY

One aspect is to manufacture an electrochemical sensor by a process of both high efficiency and high flexibility (e.g. with regard to the formation of different electrode set-ups).

One aspect is a process for manufacturing an electrochemical sensor, which includes moving a metal wire from a wire feed unit to a wire pick-up unit, the moving wire passing at least one printer $P_{cond}$ which is located in between the wire feed and wire pick-up units, and printing an ink which includes electrically conductive particles by the printer $P_{cond}$ onto discrete arrays of an electrically insulating polymer coating which is present on the metal wire.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
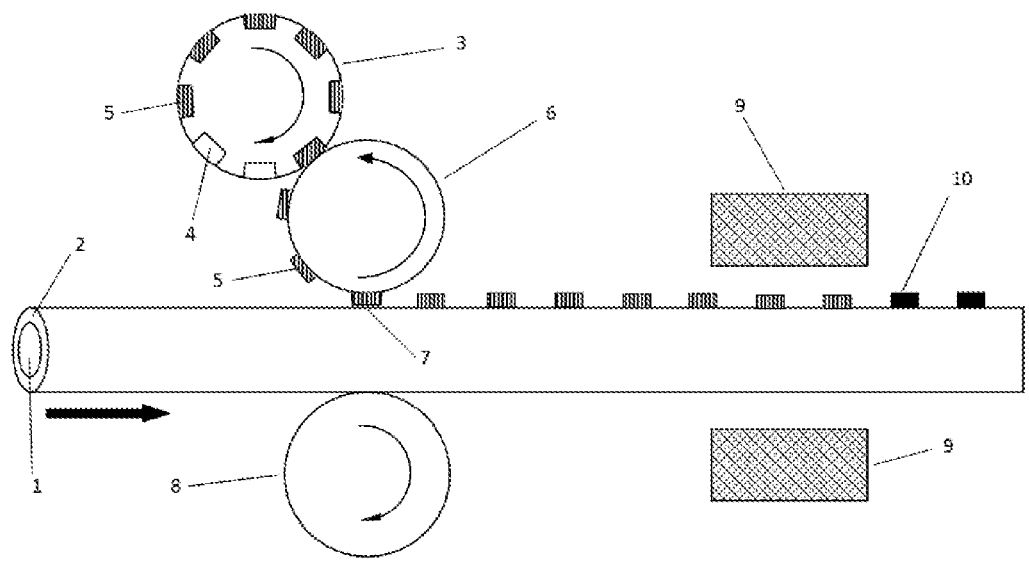
FIG. 1 illustrates printing conductive ink in accordance with one embodiment.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

The process of one embodiment is a reel-to-reel process. As a wire is moved from the wire feed unit to the wire pick-up unit and a plurality of discrete arrays of electrically conductive material are printed onto the moving wire, a high manufacturing rate is achieved. Cutting of the printed wire into individual sensor elements is carried out at a later stage. Furthermore, as the discrete printed arrays of conductive material may correspond to the final electrode pattern, removal of the conductive material at a later stage can be avoided. In addition, a variety of different electrode set-ups can be provided on the wire by the process of the present embodiments.

Typically, the wire feed unit includes a roll for unwinding the wire, while the wire pick-up unit includes a roll for rewinding the wire. The speed at which the metal wire is moved from the wire feed unit towards the wire pick-up unit may vary over a broad range. In an exemplary embodiment, the metal wire is moved at a speed of 1 to 200 m/min, in one embodiment 5 to 100 m/min. During the printing of the conductive ink onto the discrete arrays of the insulting polymer coating, the wire is moved, in one embodiment at the speed mentioned above.

Metal wires which may act as one of the electrodes of an electrochemical sensor, in one embodiment an electrochemical glucose sensor, are known to the skilled person. The metal wire may include one or more of the following metals: A noble metal (either in elementary form or as a noble-metal-based alloy); stainless steel, tantalum (either in elementary form or as a Ta-based alloy), titanium (either in elementary form or as a Ti-based alloy), a nickel- or cobalt-based alloy (such as the alloy which contains 33-37 wt % Co, 33-37 wt % Ni, 19-21 wt % Cr and 9-11 wt % Mo and is commercialized under the trade name MP35N®).

The term "noble-metal-based alloy" means that the metal of highest concentration, in at %, which is present in the alloy is a noble metal. The same applies to the other alloys. So, just as an example, the metal of highest concentration, in at %, which is present in a Ti-based alloy is Ti.

The noble metal is in one embodiment platinum, palladium, iridium, gold or silver or an alloy of at least one of these metals. A preferred noble in one embodiment metal alloy is a platinum-based alloy which contains up to 35 wt % Ir (e.g. 90 wt % Pt and 10 wt % Ir).

In one embodiment, it is also possible that the metal wire includes a metal core which is at least partially surrounded by a metal coating. Exemplary combinations of a metal core and a metal coating are the following ones: Tantalum or a Ta-based alloy as a core which is coated with platinum; tantalum or a Ta-based alloy as a core which is coated with a platinum-based alloy (e.g. a platinum-iridium alloy); a nickel- or cobalt-based alloy (e.g. MP35N®) as a core which is coated with platinum; a nickel- or cobalt-based alloy (e.g.

MP35N®) as a core which is coated with a platinum-based alloy (e.g. a platinum-iridium alloy); stainless steel as a core which is coated with platinum or a platinum-based alloy (e.g. a platinum-iridium alloy); titanium or a Ti-based alloy as a core which is coated with platinum; titanium or a Ti-based alloy as a core which is coated with a platinum-based alloy (e.g. a platinum-iridium alloy); iridium or an Ir-based alloy as a core which is coated with platinum; iridium or an Ir-based alloy as a core which is coated with a platinum-based alloy (e.g. a platinum-iridium alloy).

The metal wire may have a diameter of up to 250 μm, e.g. 50 μm to 250 μm, in one embodiment 50 μm to 180 μm, in one embodiment 90 μm to 110 μm.

The metal wires which can be used in one embodiment for manufacturing the electrochemical sensor are commercially available or can be obtained by commonly known manufacturing methods.

In the final electrochemical sensor, the metal wire may act as a working electrode. However, it is also possible that the metal wire acts as a reference or a counter electrode.

As the metal wire and the one or more printed electrodes need to be separated from each other by one or more electrically insulating materials, the metal wire is at least partially coated with an electrically insulating polymer coating at the latest when the wire reaches the printer $P_{cond}$ for applying the conductive ink. An electrically insulating polymer coating might already be present on the metal wire being released from the wire feed unit or might be applied onto the metal wire before reaching the printer $P_{cond}$. It is also possible that the metal wire which is released from the wire feed unit already includes a first electrically insulating polymer coating and a second electrically insulating polymer coating is applied before the wire reaches the conductive ink printer $P_{cond}$.

The electrically insulating polymer coating can be applied onto the metal wire by commonly known coating methods, such as die coating, dip coating, or felt coating.

The electrically insulating polymer coating might be applied to the metal wire by printing, such as pad printing or nozzle printing.

As known to the skilled person, pad printing is an indirect gravure printing method wherein ink is picked up by a flexible pad (e.g. a rubber-containing pad such as a silicone pad) and transferred to the substrate on which an image shall be printed. Due to its flexibility, the pad can adapt to the surface contour of the object when printing the image. Details about pad printing are described e.g. by R. Urbas et al., "*Pad Printing*", pp. 263-278, in "*Printing on Polymers: Fundamentals and Applications*", Ed.: J. Izdebska, S. Thomas, Elsevier, 2016.

If the insulating polymer coating is applied by nozzle printing (i.e. by a printer which ejects the ink via one or more printing nozzles), this might be an inkjet printing, an aerosol jet printing, an aerosol deposition method, a spray coating, or a micro-pen method. The inkjet printing might be a continuous inkjet printing (i.e. printing by a continuous inkjet printer) or a drop-on-demand (DOD) inkjet printing (such as thermal inkjet printing and piezoelectric inkjet printing If applied by printing, it is preferred in one embodiment that the printed polymer coating does not completely cover the metal wire so that exposed (i.e. non-coated) areas of the metal wire at pre-defined intervals in longitudinal direction of the metal wire are generated. Accordingly, if the insulating polymer coating is applied by printing, it might be preferred that unprinted (i.e. blank) areas of the metal wire at pre-defined intervals in longitudinal direction of the metal wire remain after the printing of the insulating polymer coating. As the exposed areas of the metal wire are already generated during the printing step, removal of the insulating polymer coating (e.g. by laser ablation or other physical or chemical ablation methods) at a later stage might be avoided or the extent of the ablation treatment might at least be significantly reduced.

The electrically insulating polymer coating might be a single-layered or a multi-layered coating. If multi-layered, each layer of the insulating polymer coating may include one or more of the polymers mentioned further below.

The electrically insulating polymer coating might have a thickness of up to 75 μm, e.g. 5 μm to 75 μm, in one embodiment 10 μm to 30 μm.

For applying an electrically insulating polymer coating, at least one coating unit, in one embodiment at least one printer $P_{ins}$ (e.g. a pad printer or a nozzle-containing printer such as an inkjet printer), might be located between the wire feed unit and the printer $P_{cond}$ which prints the conductive ink onto the electrically insulating polymer coating. In other words, if the insulating polymer coating is applied by a printer $P_{ins}$, the printer $P_{ins}$ might be located upstream of the conductive ink printer $P_{cond}$ (and downstream the wire feed unit). However, in the process of one embodiment, it is also possible that the electrically insulating polymer coating is applied by printing in a separate reel-to-reel unit (i.e. the printer $P_{ins}$ is located at a separate reel-to-reel unit) and the wire being coated with the insulating polymer coating is subsequently transferred to the reel-to-reel unit where the one or more printers $P_{cond}$ are located.

"$P_{ins}$" refers to a printer which is used for applying the electrically insulating polymer coating. If the printer is a pad printer, it is referred to as "$PP_{ins}$". If the printer is a nozzle-containing printer (e.g. an inkjet printer), it is referred to as "$NP_{ins}$". "$P_{cond}$" refers to the printer which prints the conductive ink (i.e. the ink including electrically conductive particles) onto the electrically insulating polymer coating.

Appropriate polymers for providing electrically insulating coatings are known to the skilled person. The electrically insulating polymer coating may include one or more of the following polymers: a polyurethane, a fluoropolymer (such as a tetrafluoroethylene homopolymer (PTFE) or a copolymer thereof such as an ethylene-tetrafluoroethylene copolymer (ETFE)), a polyimide, a polyethylene, or a polypropylene, or a blend of two or more of these polymers. Each of these polymers might be a homopolymer or a copolymer.

Appropriate inks for applying these polymers by printing (in one embodiment pad printing or nozzle printing) are commercially available.

If the electrically insulating polymer coating is applied by a printer $P_{ins}$ which is located in between the wire feed unit and the printer $P_{cond}$ (i.e. the printer which prints the conductive ink onto the electrically insulating polymer coating), it might be preferred that at least one thermal heating unit (e.g. an oven) is located between $P_{ins}$ and $P_{cond}$. When passing the thermal heating unit, solvent of the ink may evaporate and/or curing of the insulating polymer might be accomplished.

The metal wire which reaches the printer $P_{cond}$ might be completely coated with the insulating polymer coating or might contain one or more areas on which no insulating polymer coating is present (these non-coated areas being accessible to the analyte in the final sensor). If completely coated by the insulating polymer coating, an ablation treatment (e.g. laser ablation) might be carried out at a later stage so as to expose the metal wire in one or more defined areas and thereby making the metal wire accessible to an analyte in these exposed areas. The ablation treatment might be carried out in an ablation unit which is located downstream the conductive ink printer $P_{cond}$. In one embodiment, the ablation unit includes a laser.

As indicated above, an ink which includes electrically conductive particles is printed by the printer $P_{cond}$ onto discrete arrays of an electrically insulating polymer coating which is present on the metal wire.

Typically, the ink is printed at pre-defined time intervals so that a well-defined and uniform configuration of the printed arrays is achieved over the length of the wire.

By this printing step and a subsequent thermal treatment step, discrete electrically conductive solid coatings are formed on the electrically insulating polymer coating. In the final electrochemical sensor, these discrete solid coatings may represent the electrodes (e.g. the reference electrode and the counter electrode).

In the process of one embodiment, just one printer $P_{cond}$ might be located between the wire feed and pick-up units. However, it might be preferred that at least two printers $P_{cond}$ are located between the wire feed and pick-up units. If two or more printers $P_{cond}$ are present, more complex electrode set-ups might be printed in a single pass. Just as an example, a first printer $P_{cond}$ might print the conductive ink onto the upper half of the polymer-coated wire, while a second printer $P_{cond}$ prints the conductive ink onto the lower half of the polymer-coated wire, thereby obtaining a sensor having a multiple-electrode (e.g. three-electrode) set-up (i.e. the metal wire as a first electrode and two printed electrodes on opposing sides of the polymer-coated wire).

The printer $P_{cond}$ which prints the conductive ink onto discrete arrays of the electrically insulating polymer coating might be a pad printer $PP_{cond}$ which includes one or more flexible pads; or a nozzle printer $NP_{cond}$ which includes at least one printing nozzle.

Typically, the pad printer $PP_{cond}$ includes at least one flexible pad which repeatedly picks up the ink containing electrically conductive particles and prints the ink onto discrete arrays of the electrically insulating polymer coating which is present on the metal wire. By this pad-printing step and a subsequent thermal treatment step, discrete electrically conductive solid coating are formed at pre-defined intervals on the electrically insulating polymer coating.

Appropriate flexible pads for pad printing are known to the skilled person. The pad might be a stamp or a brush. The pad might include a silicone rubber. However, other flexible materials (e.g. elastomers other than silicone rubber) might be used as well.

The ink to be picked up by the pad might be provided in depressions of a plate (also known as cliché). The flexible pad is brought into contact with the ink and transfers the ink from the depressions to the electrically insulating polymer coating.

In one embodiment, the ink to be picked up by the flexible pad might be printed (e.g. screen-printed) onto a depression-free area of a flat plate where it is picked up by the pad and transferred to the electrically insulating polymer coating.

In another exemplary embodiment, the flexible pad is a roll which picks up ink from an engraved roll. Typically, both rolls are rotating in opposite directions during the pad printing step.

In another exemplary embodiment, two more flexible pads are positioned in a rotatable pad holder (e.g. a circular pad holder). For picking up the ink and printing the ink onto the electrically insulating polymer coating, the pad holder rotates. During one revolution of the pad holder, each of the pads positioned in the pad holder picks up ink and prints the ink onto the electrically insulating polymer coating. The ink to be picked up by the pads might be provided in wells of an ink-delivering roll (e.g. ink-delivering engraved roll). The pad holder and the ink-delivering roll rotate in opposite directions. When one of the flexible pads of the pad holder comes into contact with one of the ink-filled wells of the ink-delivering roll, the flexible pad picks up the ink. Upon further rotation of the pad holder, each pad that has picked up ink from the counter-rotating ink-delivering roll comes into contact with a defined area of the electrically insulating polymer coating and transfers the ink to the area.

The rotating pad holder may include a cam. As known to the skilled person, a cam is a rotating or sliding part which is used for transforming rotary motion into linear motion. The cam can be a part of a rotating wheel (e.g. an eccentric wheel) or shaft (e.g. a camshaft). Due to the interaction between the cam and the pads, a back-and-forth motion of each of the pads is achieved. The pads might be spring-loaded pads. If pushed forward, the pad may pick up ink from the ink-delivering roll or may transfer the picked-up ink to the electrically insulating polymer coating. If a pad just being in contact with the insulating polymer coating on the metal wire moves back, the ink transfer from the pad to the polymer coating is interrupted but will be repeated during the next revolution of the rotating pad holder.

A nip roll might be used to improve wire guidance and provide a counter force to the force applied by the pad to the wire. The nip roll is typically positioned such that the pad in its printing position (i.e. when printing the ink onto the insulating polymer coating) and the nip roll are located on opposing sides of the wire.

The nozzle-containing printer can be an inkjet printer, an aerosol jet printer, a printer for spray coating, a printer for aerosol deposition, or a printer for micro-pen printing. These nozzle printing methods are known to the skilled person.

The inkjet printer can be a continuous inkjet printer ("CIJ printing") or a drop-on-demand inkjet printer ("DOD" inkjet printing).

In a continuous inkjet printer, ink droplets are constantly generated, controlled by a high-pressure pump vibrating the nozzle with a piezoelectric crystal. The generated ink droplets are selectively charged by signals from the printer. Charged droplets are deflected into a gutter for recirculation, while the uncharged droplets are ejected onto the substrate to form an image.

Different from a continuous inkjet printer, a drop-on-demand (DOD) inkjet printer ejects the ink only when it is required. DOD inkjet printers are e.g. thermal inkjet printers and piezoelectric inkjet printers. In a thermal inkjet printer, the ink in the ink chamber is rapidly heated up to a vaporization temperature. Due to vaporisation, a bubble is promptly generated at the surface of a heating element, causing a pressure pulse to eject the ink droplets through the nozzle. In a piezoelectric printer, a piezo-ceramic material is used for generating ink droplets. In response to an electric impulse, the piezo-ceramic material deforms, thereby generating a pressure wave by which the ink is ejected through the printing nozzle.

In aerosol jet printing, aerodynamic focusing is used to accurately deposit the ink on a substrate. The ink is placed into an atomizer which creates a dense mist of droplets. The aerosol mist is then delivered to the deposition head where it is focused by a sheath gas, which surrounds the aerosol. When the sheath gas and aerosol pass through the nozzle, they accelerate and the aerosol droplet stream flows inside the sheath gas. The resulting high velocity stream remains focused until reaching the substrate.

The size of the discrete arrays onto which the conductive ink is printed might be adjusted by parameters which are known to the skilled person, e.g. by the dimensions of the printing nozzle or the size of the printing pad.

Each of the discrete printed arrays may have a size of e.g. 100 μm² to 10000 μm².

Each of the discrete printed arrays (i.e. the discrete arrays of the insulating polymer coating on which the conductive ink is printed) may or may not extend over the whole circumference of the electrically insulating polymer coating. In one embodiment, each of the discrete printed arrays has an extension in circumferential direction of the insulating polymer coating which is less than 50%, e.g. 5% to 45%, in one embodiment 10% to 40%, of the circumference of the electrically insulating polymer coating. If the metal wire on which the insulating polymer coating is present is divided by an imaginary plane along the longitudinal axis of the wire into an upper half and a lower half, a first set of discrete printed arrays might be present on the upper half while a second set of discrete nozzle-printed arrays might be present on the lower half. The first set of discrete printed arrays might be printed with a first printer $P_{cond}$, while the second set of discrete printed arrays might be printed with a second printer $P_{cond}$. If discrete arrays having a relatively small extension in circumferential wire direction are printed on upper and lower halves of the polymer-coated wire, sensors having a multiple-electrode (e.g. three-electrode) configuration can be efficiently prepared. Furthermore, such a configuration with electrodes on opposing halves of the wire may facilitate the formation of an electrical connection between the electrodes and the sensor electronics (such as a potentiostat).

The ink which is printed on the discrete arrays of the electrically insulating polymer coating includes electrically conductive particles.

Conductive inks for preparing electrodes of electrochemical sensors (e.g. glucose sensors) are known to the skilled person and are commercially available or can be prepared by commonly known methods.

The electrically conductive particles might be metal particles, carbon-based particles such as nanotubes or graphene, or other any combination thereof.

Exemplary metal particles are noble-metal-containing particles, e.g. silver-containing particles, Pt-containing particles, and Au-containing particles. In one embodiment, the ink includes metallic silver (Ag) particles and silver chloride (AgCl) particles (i.e. a Ag/AgCl-containing ink).

The ink may have a solids content of 40-90 wt %, in one embodiment 55-85 wt %. The ink may have a viscosity, 25° C., Brookfield #14 spindle, 10 rpm, of 150,000 cps or less, in one embodiment 120,000 cps or less.

If a Ag/AgCl-containing ink is used, it might be preferred that the weight ratio of Ag to AgCl is from 50/50 to 95/5, in one embodiment 65/35 to 90/10.

The ink may additionally include a binder. Appropriate binders for conductive inks (such as Ag/AgCl-containing inks) are known to the skilled person. The binder might be a polymer or a precursor thereof (e.g. oligomers which may react to a polymer) that can be cured by thermal treatment or radiation treatment (e.g. UV treatment) to a thermoset. In one embodiment, the binder is a polymer or a precursor of a polymer which is also present in the electrically insulating polymer coating. Just as an example, if the electrically insulating polymer coating includes a polyurethane, it might be preferred that the binder being present in the ink is also a polyurethane or a precursor of a polyurethane. Accordingly, the binder of the conductive ink may include one or more of the following polymers or precursors thereof: a polyurethane, a fluoropolymer (such as a tetrafluoroethylene homopolymer (PTFE) or a copolymer thereof such as an ethylene-tetrafluoroethylene copolymer (ETFE)), a polyimide, a polyethylene, or a polypropylene, or a blend of two or more of these polymers. Each of these polymers might be a homopolymer or a copolymer.

The ink might be a solvent-based ink. Appropriate organic solvents for printing inks are known to the skilled person. In one embodiment, the ink has a water content of less than 15 vol %; in one embodiment, the ink is water-free.

In one embodiment, the ink which has been printed onto discrete arrays of the insulating polymer coating is subjected to a thermal treatment so that remaining solvent evaporates and, if present, curing of the binder is accomplished. Furthermore, thermal treatment may assist in sintering the electrically conductive particles, thereby improving conductivity. Thermal treatment might be carried out at a temperature of 350° C. or less, e.g. in a thermal treatment unit such as an oven which is located downstream the conductive ink printer $P_{cond}$.

By the thermal treatment, discrete electrically conductive solid coatings on the insulating polymer coating are obtained. Each of the discrete electrically conductive solid coatings may have a thickness of 3 μm to 50 μm, in one embodiment 5 μm to 20 μm. In the final electrochemical sensor, the discrete electrically conductive solid coatings may act as electrodes (e.g. as a reference electrode and a counter electrode).

Optionally, the process of one embodiment may include an ablation treatment step wherein the electrically insulating polymer coating is removed in one or more pre-defined areas, thereby exposing the metal wire in the one or more pre-defined areas (and making the metal wire accessible to an analyte in these exposed areas). The ablation treatment can be a physical ablation, in one embodiment laser ablation, or a chemical ablation.

The ablation treatment can be carried out in an ablation treatment unit. In one embodiment, the ablation treatment unit includes a laser for selectively removing the electrically insulating polymer coating in one or more pre-defined areas. The ablation treatment unit might be positioned downstream or upstream of the printer $P_{cond}$ (i.e. the printer which prints the conductive ink onto discrete arrays of the the electrically insulating polymer coating).

As already mentioned above, it might be preferred that both the insulating polymer coating and the conductive ink are applied by printing. By this embodiment, an ablation treatment might be avoided or its extent might at least be significantly reduced.

For obtaining a sensor element having a two-electrode or multiple electrode (e.g. three-electrode) set-up, the wire is typically cut into individual pieces such that each piece of wire includes the desired number of discrete electrically conductive solid coatings on the electrically insulating polymer coating. The wire cutting unit might be downstream of the wire pick-up unit. In between the wire feed and pick-up units, no wire cutting unit is present (i.e. no wire cutting takes place in between the wire feed and pick-up units).

The process of one embodiment will be described in further detail by the following exemplary embodiment illustrated in FIG. 1. In the exemplary embodiment of FIG. 1, the conductive ink is printed by pad printing. A metal wire 1 on which an electrically insulating polymer coating 2 has already been applied is unwound from a wire feed roll (not illustrated in FIG. 1) and is moved towards a wire pick-up roll (not illustrated in FIG. 1). The arrows in FIG. 1 indicate the moving direction of the wire 1 and the rotation directions of the rolls. An ink-delivering roll 3 includes wells 4, some of these wells 4 being filled with an ink 5. The ink 5 includes electrically conductive particles. Just as an example, the ink 5 may contain Ag particles and AgCl particles. The ink-delivering roll 3 and a circular pad holder 6 containing several flexible pads (e.g. pads made of silicone rubber) are rotating in opposite directions. The flexible pads which are positioned in the pad holder 6 are not illustrated in FIG. 1. If one of the pads of the rotating pad holder 6 comes into contact with one of the ink-filled wells 4 of ink-delivery roll 3, the pad picks up the ink 5. Upon further rotation of pad holder 6, the pad which has picked up ink 5 comes into contact with the electrically insulation polymer coating 2. The picked up ink 5 is transferred from the pad to a discrete array 7 of the electrically insulation polymer coating 2. During a single revolution of the pad holder 6, each pad picks up ink 5 and prints it on a discrete array 7 of the insulating polymer coating 2. A nip roll 8 improves guidance of the wire 1 and provides a counter force to the pad holder 6. As the wire 1 moves towards the wire pick-up unit, it passes an oven 9 where the ink 5 which has been pad-printed onto the discrete arrays 7 of the polymer coating 2 are subjected to a thermal treatment and transformed into discrete solid electrically conductive coatings 10 which may act as electrodes in the final electrochemical sensor.

Figure 2:
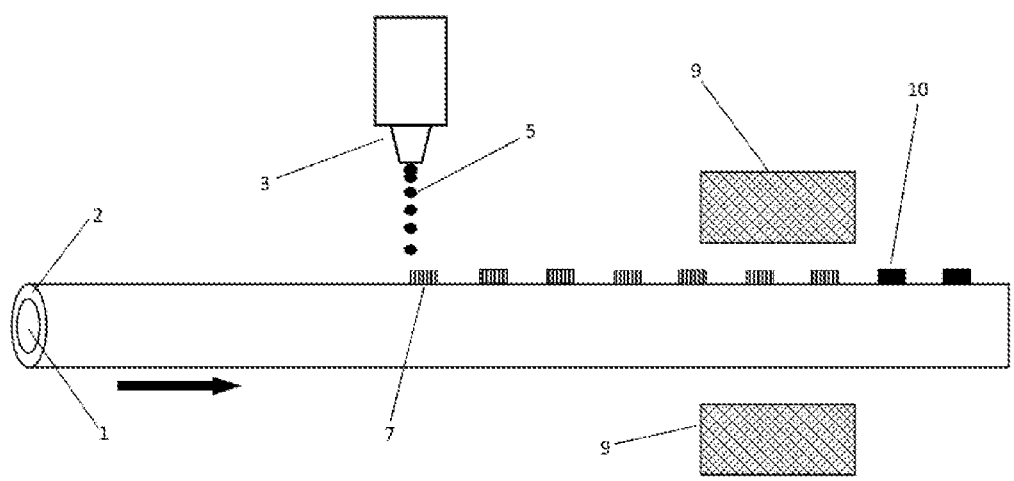
FIG. 2 illustrates printing conductive ink in accordance with one embodiment.

An exemplary embodiment wherein the conductive ink is printed onto the discrete arrays of the insulating polymer coating via nozzle printing is illustrated in FIG. 2. A metal wire 1 on which an electrically insulating polymer coating 2 has already been applied is unwound from a wire feed roll (not illustrated in FIG. 1) and is moved towards a wire pick-up roll (not illustrated in FIG. 1). The arrow in FIG. 2 indicates the moving direction of the wire 1. The wire passes a printer which includes at least one printing nozzle 3 by which an ink 5 including electrically conductive particles is printed onto discrete arrays 7 of the insulating polymer coating 2. The discrete arrays 7 on which the ink 5 has been printed are located at pre-defined intervals in longitudinal direction of the wire. The wire 1 is moved through a thermal treatment unit 9 (e.g. an oven), thereby obtaining discrete electrically conductive solid coatings 10 which may act as electrodes in the final electrochemical sensor.

Figure 3:
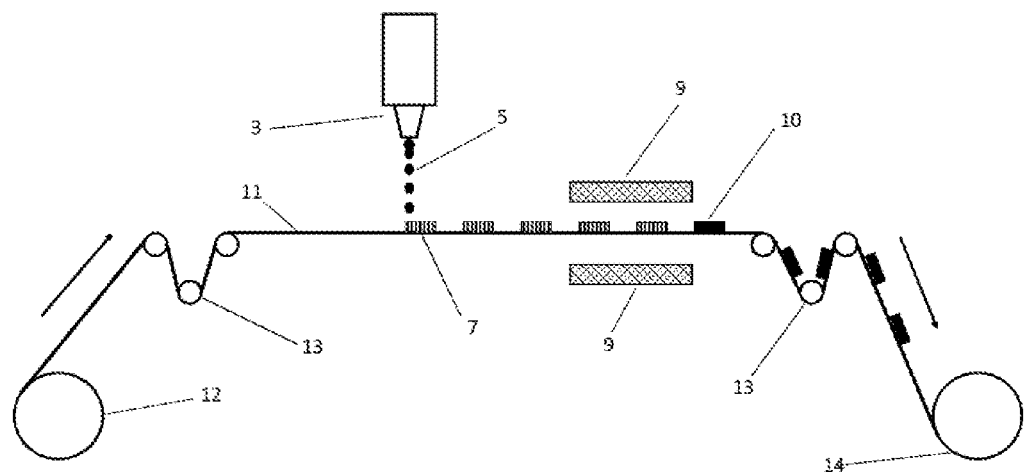
FIG. 3 illustrates printing conductive ink in accordance with one embodiment.

Just like FIG. 2, FIG. 3 illustrates the exemplary embodiment which uses nozzle printing, but additionally illustrates the wire feed and wire pick-up units. An elongated body 11 which is made of the metal wire 1 and the insulating polymer coating 2 is released from a wire feed unit 12. The arrows in FIG. 2 indicate the moving direction of the elongated body 11. Tension of the elongated body 11 can be adjusted by guide or tension rolls 13. As already illustrated in FIG. 1, the elongated body 11 passes a printer which includes at least one printing nozzle 3 by which an ink 5 including electrically conductive particles is printed onto discrete arrays 7 of the insulating polymer coating 2. The discrete arrays 7 on which the ink 5 has been printed are located at pre-defined intervals in longitudinal direction of the elongated body 11. The elongated body 11 is moved through a thermal treatment unit 9 (e.g. an oven), thereby obtaining discrete electrically conductive solid coatings 10 which may act as electrodes in the final electrochemical sensor. In the wire pick up unit 14, the elongated body is rewound.

Figure 4:
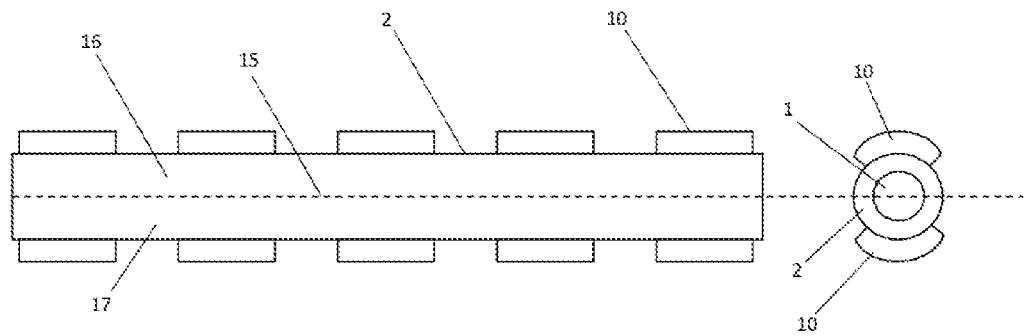
FIG. 4 illustrates an insulating polymer coating on which discrete electrically conductive solid coatings have been formed in accordance with one embodiment.

FIG. 4 illustrates an insulating polymer coating 2 (being present on a metal wire 1) on which discrete electrically conductive solid coatings 10 have been formed by printing and subsequent thermal treatment (right half of FIG. 2: view in longitudinal direction of the wire; left half of FIG. 2: view in cross-section of the wire). If the wire 1 having applied thereon an insulating polymer coating 2 is divided by an imaginary plane 15 along its longitudinal axis into an upper half 16 and a lower half 17, a first set of discrete electrically conductive solid coatings 10 is exclusively present on the upper half 16 while a second set of discrete electrically conductive solid coatings 10 is exclusively present on the lower half 17. Each of the discrete solid coatings 10 has an extension in circumferential direction of the insulating polymer coating 2 which is less than half of the circumference of the insulating polymer coating 2. Each of the discrete solid coatings 10 on the upper half 16 of the wire is directly opposed by a discrete solid coating 10 on the lower half 17 of the wire.

Figure 5:
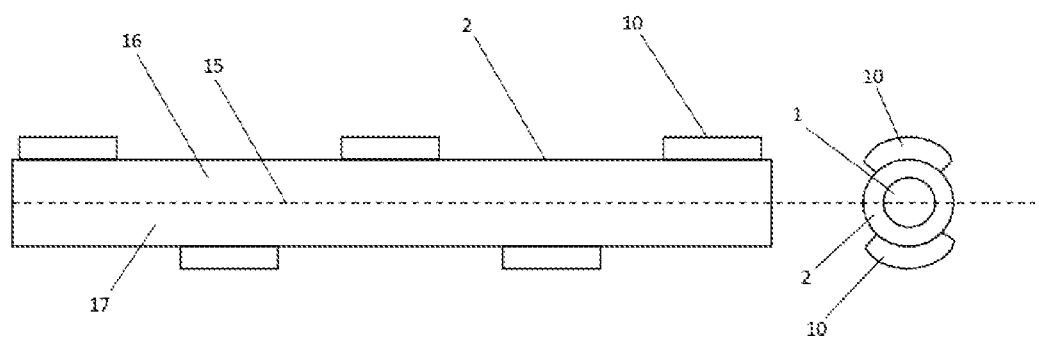
FIG. 5 illustrates an insulating polymer coating on which discrete electrically conductive solid coatings have been formed in accordance with one embodiment.

Similar to FIG. 4, FIG. 5 illustrates an insulating polymer coating 2 (being present on a metal wire 1) on which discrete electrically conductive solid coatings 10 have been formed by printing and subsequent thermal treatment (right half of FIG. 2: view in longitudinal direction of the wire; left half of FIG. 2: view in cross-section of the wire). If the wire 1 having applied thereon an insulating polymer coating 2 is divided by an imaginary plane 15 along its longitudinal axis into an upper half 16 and a lower half 17, a first set of discrete solid coatings 10 is exclusively present on the upper half 16 while a second set of discrete solid coatings is exclusively present on the lower half 17. Different from the exemplary embodiment of FIG. 4, the sets of discrete solid coatings 10 on the upper half 16 and lower half 17 are shifted relative to each other such that a discrete solid coating 10 on the upper half 16 is not directly opposed by a discrete solid coating 10 on the lower half 17.

By the manufacturing process of one embodiment, a wire-based electrochemical sensor having a specific electrode set-up is obtainable.

According to a further embodiment, an electrochemical sensor includes
  an elongated body which includes
    a metal wire,
    an electrically insulating polymer coating on the metal wire,
    two or more discrete electrodes which are present on the electrically insulating polymer coating,
wherein each of the two or more discrete electrodes has an extension in circumferential direction of the elongated body which is less than 50% of the circumference of the elongated body.

In one embodiment, the electrochemical sensor is obtainable by the process as described above.

In one embodiment, one of the discrete electrodes is exclusively located on the upper half of the elongated body (and does therefore not extend to the lower half of the elongated body), while the other discrete electrode is exclusively located on the lower half of the elongated body (and does therefore not extend to the upper half of the elongated body). In other words, if the elongated body is divided by an imaginary plane along its longitudinal axis into an upper half and a lower half, one of the discrete electrodes is exclusively present on the upper half while the other discrete electrode is exclusively present on the lower half. If discrete electrodes having a relatively small extension in circumferential direction of the elongated body are provided on upper and lower halves of the elongated body, a sensor having a very efficient multiple-electrode (e.g. three-electrode) set-up is obtained. Furthermore, such a configuration with electrodes on opposing halves of the elongated body may facilitate the formation of an electrical connection between the electrodes and the sensor electronics (such as a potentiostat). In one embodiment, each of the two or more discrete electrodes has an extension in circumferential direction of the elongated body which is 5% to 45%, in one embodiment 10% to 40%, of the circumference of the electrically insulating polymer coating One of the discrete electrodes may act as a reference electrode, while the other discrete electrode may act as a counter electrode. The metal wire may act as the working electrode.

In one embodiment, the metal wire is only partially coated by the electrically insulating polymer coating. The one or more areas of the metal wire which are not coated by the insulating polymer coating are therefore accessible by an analyte.

Optionally, an enzyme (e.g. an oxidase enzyme such as glucose oxidase) or a polymer membrane including the enzyme might be present on the one or more areas of the metal wire which are not coated by the insulating polymer coating. However, it is also possible that a non-enzymatic material which may promote a redox reaction with an analyte is applied onto the one or more areas of the metal wire which are not coated by the insulating polymer coating.

With regard to preferred metal wires, reference can be made to those mentioned above for the manufacturing process. Accordingly, as already outlined above, the metal wire may include a noble metal (either in elementary form or as a noble-metal-based alloy); stainless steel, tantalum (either in elementary form or as a Ta-based alloy), titanium (either in elementary form or as a Ti-based alloy), a nickel- or cobalt-based alloy (such as the alloy which contains 33-37 wt % Co, 33-37 wt % Ni, 19-21 wt % Cr and 9-11 wt % Mo and is commercialized under the trade name MP35N®). The metal wire may have a diameter of up to 250 µm, e.g. 50 µm to 250 µm, in one embodiment 50 µm to 180 µm, in one embodiment 90 µm to 110 µm.

With regard to preferred electrically insulating polymer coatings, reference can be made to those mentioned above for the manufacturing process. Accordingly, the electrically insulating polymer coating may include a polyurethane, a fluoropolymer (such as a tetrafluoroethylene homopolymer (PTFE) or a copolymer thereof such as an ethylene-tetrafluoroethylene copolymer (ETFE)), a polyimide, a polyethylene, or a polypropylene, or a blend of two or more of these polymers. Each of these polymers might be a homopolymer or a copolymer. The electrically insulating polymer coating might have a thickness of up to 75 µm, e.g. 5 µm to 75 µm, in one embodiment 10 µm to 30 µm.

Each of the at least two discrete electrodes on the insulating polymer coating may contain electrically conductive particles. Again, with regard to preferred electrically conductive particles, reference can be made to those mentioned above for the manufacturing process. The electrically conductive particles might be metal particles, carbon-based particles such as nanotubes or graphene, or any combination thereof. Exemplary metal particles are noble-metal-containing particles, e.g. silver-containing particles, Pt-containing particles, and Au-containing particles. In one embodiment, the discrete electrodes include metallic silver (Ag) particles and silver chloride (AgCl) particles.

Optionally, the discrete electrodes may include one or more of the following polymers: a polyurethane, a fluoropolymer (such as a tetrafluoroethylene polymer), a polyimide, a polyethylene, a polypropylene. Each of these polymers might be a homopolymer or a copolymer. It might be preferred that the polymer being present in the discrete electrodes is the polymer which is present in the electrically insulating polymer coating. Just as an example, if the electrically insulating polymer coating includes a polyurethane, it might be preferred that the polymer being present in the discrete electrodes is a polyurethane as well. If a polymer is present in the electrodes, a sufficiently high concentration of electrically conductive particles is selected so that the composite of conductive particles and polymer is still conductive.

As already mentioned above, each of the at least two discrete electrodes may have a thickness of 3 µm to 50 µm, in one embodiment 5 µm to 20 µm. Furthermore, each of the two discrete electrodes may have a size of 100 µm$^2$ to 10000 µm$^2$.

In one embodiment, the electrochemical sensor described above is used as a glucose sensor, i.e. for monitoring glucose concentration; an oxygen sensor; a pH sensor; or a lactose sensor.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:

1. A process for manufacturing an electrochemical sensor, comprising:
   moving a metal wire from a wire feed unit to a wire pick-up unit, the moving wire passing at least one printer $P_{cond}$ which is located in between the wire feed and wire pick-up units;
   printing an ink which comprises electrically conductive particles by the printer $P_{cond}$ onto discrete arrays of an electrically insulating polymer coating which is present on the metal wire;
   wherein the metal wire comprises a working electrode of the electrochemical sensor; and
   cutting the metal wire into individual pieces at a wire cutting unit that is located downstream of the wire pick-up unit;
   wherein the discrete arrays have a size of 100 µm$^2$ to 10000 µm$^2$.

2. The process according to claim 1, wherein the printer $P_{cond}$ is a pad printer $PP_{cond}$ which comprises one or more flexible pads.

3. The process of claim 1, wherein the metal wire is moved at a speed of 1 m/min to 200 m/min.

4. The process of claim 1, wherein the electrically insulating polymer coating is already present on the metal wire being released from the wire feed unit; or the electrically insulating polymer coating is applied at a coating or printing unit which is located downstream the wire feed unit and upstream the printer $P_{cond}$.

5. The process of claim 1, wherein the electrically insulating polymer coating is applied by pad printing or nozzle printing.

6. The process of claim 2, wherein the one or more flexible pads of the pad printer $PP_{cond}$ are repeatedly picking up the ink which contains the electrically conductive particles and print the ink onto the discrete arrays of the electrically conductive polymer coating.

7. The process according to claim 1, wherein the printer $P_{cond}$ is a nozzle printer $NP_{cond}$ which comprises at least one printing nozzle.

8. The process of claim 1, further comprising coating the metal wire with the electrically insulating polymer coating such that a first set of the discrete arrays on which the ink has been printed is present on a upper half of the metal wire while a second set of discrete arrays on which the ink has been printed is present on a lower half of the wire.

9. The process of claim 1, wherein the ink which has been printed on the discrete arrays is subjected to a thermal treatment, thereby obtaining discrete electrically conductive solid coatings which comprise the electrically conductive particles.

10. The process of claim 7, wherein the nozzle printer $NP_{cond}$ is an inkjet printer, an aerosol jet printer, a printer for spray coating, a printer for aerosol deposition, or a printer for micro-pen printing.

11. The process according to claim 1, wherein the metal wire has a diameter of 50 μm to 250 μm.

* * * * *